United States Patent [19]
Le Couedic et al.

[11] Patent Number: 6,090,113
[45] Date of Patent: Jul. 18, 2000

[54] ADJUSTABLE OSTEOSYNTHESIS SYSTEM OF THE RACHIS

[75] Inventors: Régis Le Couedic, Saint Medard en Jalles; Frédéric Conchy, Bordeaux, both of France

[73] Assignee: Stryker France S.A., France

[21] Appl. No.: 09/331,946

[22] PCT Filed: Dec. 23, 1997

[86] PCT No.: PCT/FR97/02398

§ 371 Date: Jun. 28, 1999

§ 102(e) Date: Jun. 28, 1999

[87] PCT Pub. No.: WO98/29046

PCT Pub. Date: Jul. 9, 1998

[30]   Foreign Application Priority Data

Dec. 27, 1996 [FR]   France ................................. 96 16115

[51] Int. Cl.[7] ................................................. A61B 17/56
[52] U.S. Cl. ............................................... 606/61; 606/90
[58] Field of Search .................... 606/61, 90, 57

[56]   References Cited

U.S. PATENT DOCUMENTS 5,395,370   3/1995   Muller et al. .
5,849,012  12/1998   Abboudi ..................................... 606/57

FOREIGN PATENT DOCUMENTS 8712943  11/1987   Germany .
9112466  12/1991   Germany .
WO9002527  3/1990   WIPO .

Primary Examiner—Michael Buiz
Assistant Examiner—Julian W. Woo
Attorney, Agent, or Firm—Blakely Sokoloff Taylor & Zafman

[57]   ABSTRACT

According to an embodiment of the invention, an apparatus is provided that includes positioning equipment for an osteosynthesis system for a spinal column. The positioning equipment includes two elongate anchoring members each designed to be anchored in a vertebra of the column, and an elongate anchoring linking element designed to connect the anchoring members together. The system is designed to have an unlocked configuration in which each anchoring member can turn with respect to the anchoring linking element about a first axis perpendicular to a longitudinal direction of the anchoring member and perpendicular to a longitudinal direction of the anchoring linking element. The system is also designed to have a locked configuration in which each anchoring member is rigidly fixed to the anchoring linking element. The equipment also includes to arms designed to be fixed removably to the two respective anchoring members and an elongate arm linking element designed to connect part of each arm together. The arm linking element is designed to connect the arm parts, defining an extremum for the mutual separation of the arm parts. The arm linking element includes at least one rack which has teeth designed to mesh with one of the arm parts. The rack or racks being fixed, with the ability to rotate, to the other arm part.

16 Claims, 4 Drawing Sheets

FIG_1

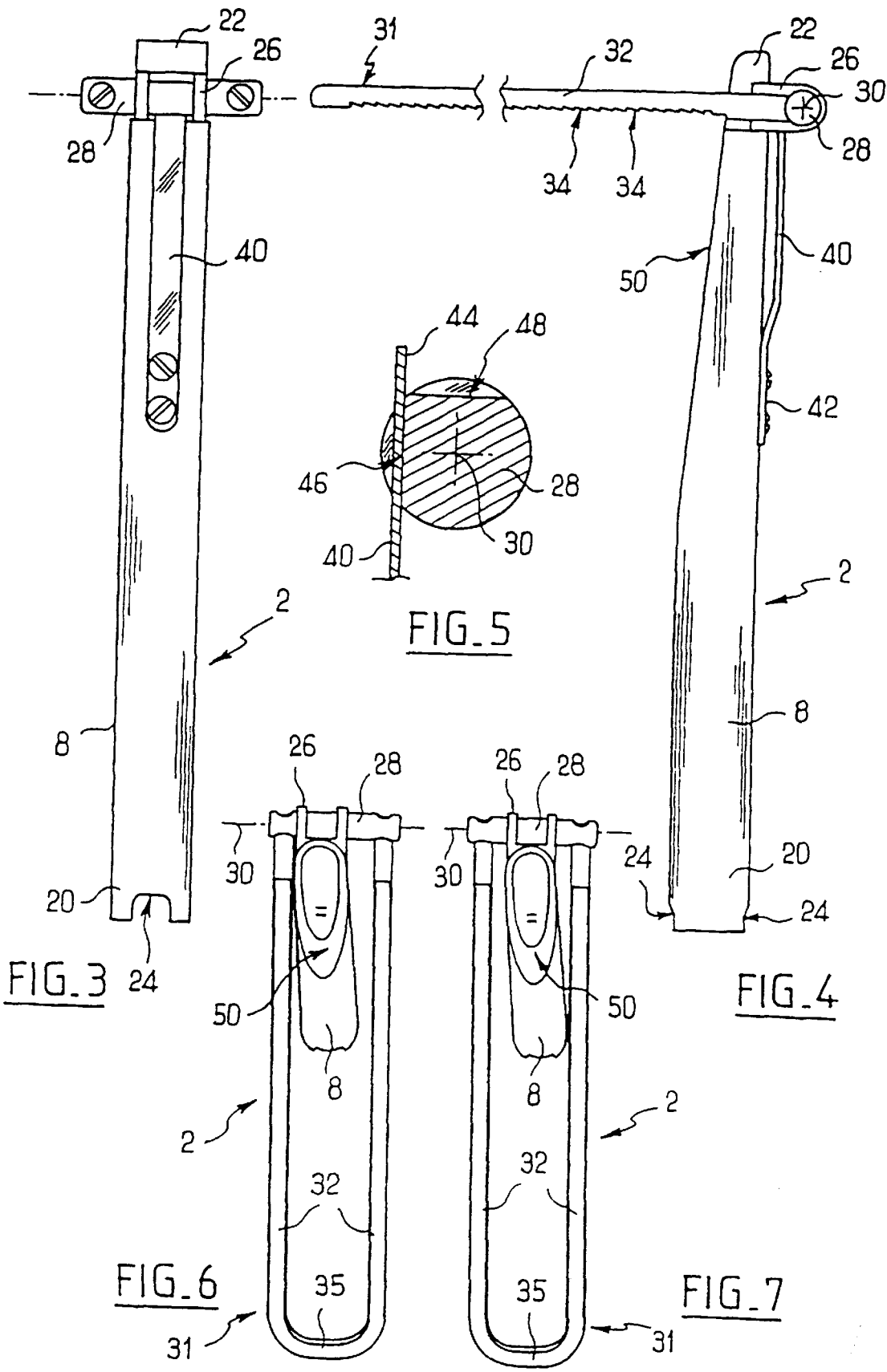

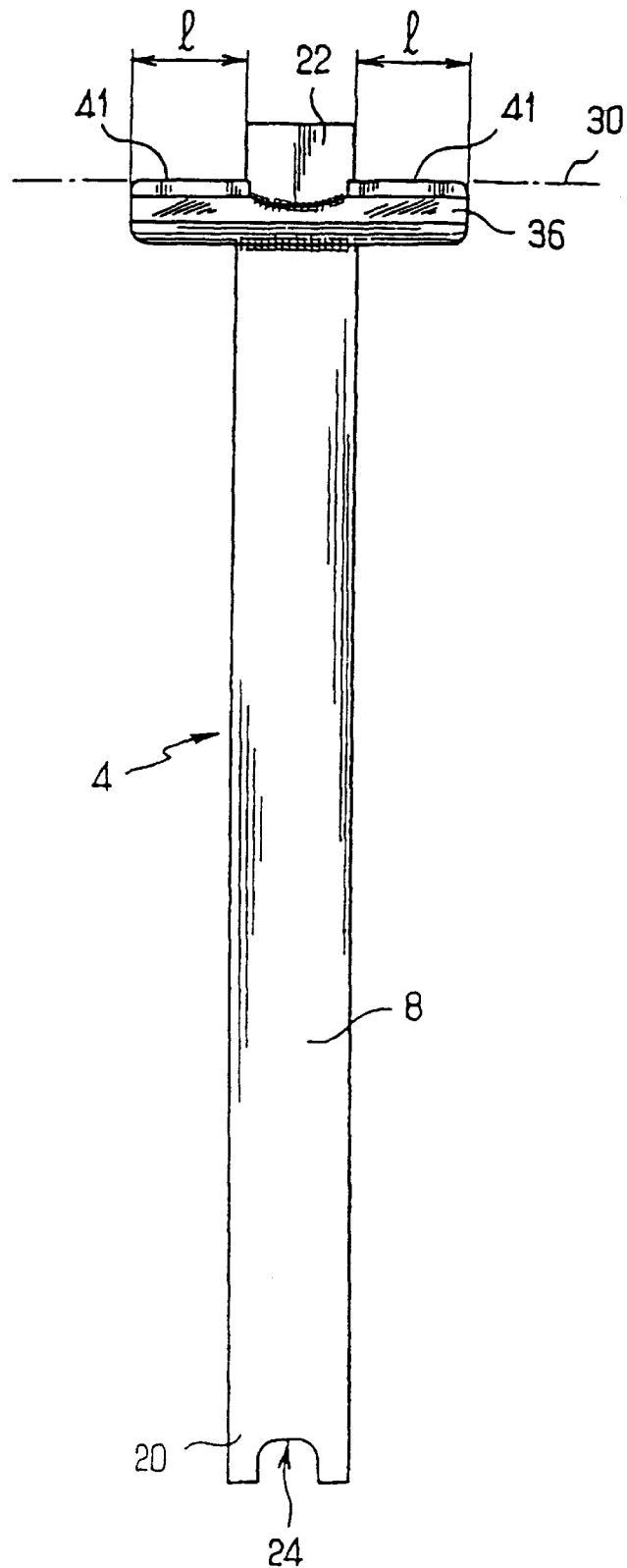
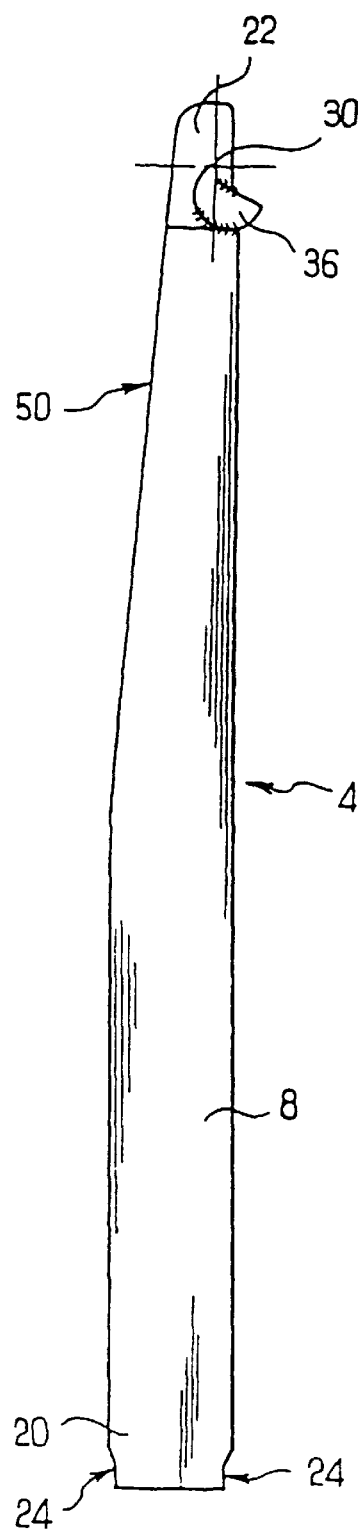
FIG_8  FIG_9

ADJUSTABLE OSTEOSYNTHESIS SYSTEM OF THE RACHIS

The invention relates to osteosynthesis systems for the spinal column and to positioning equipment for such systems.

Document FR-2 659 546 discloses an osteosynthesis system for a spinal column comprising several pedicle screws intended to be anchored in vertebrae of the spinal column and a linking rod designed to connect the pedicle screws rigidly together. Such a system is used particularly in the event of a simple or multiple fracture of one or more vertebrae of the spinal column. The fracture may have various configurations and entail corrective movements in order to recover the original morphology of the spine, particularly as far as the lordosis or cyphosis curvatures are concerned. To achieve this, each pedicle screw comprises a spherical collar slipped onto the rod so that it can slide and housed in a recess in the head of the pedicle screw while at the same time being free to move in this recess. Once the screws have been anchored into the vertebrae, each pedicle screw can therefore be placed in any position whatever along the rod, and at any orientation whatever with respect to the rod. The head of the screw comprises a locking member that allows the screw, the collar and the rod to be rigidly immobilized with respect to each other so as to rigidly fix the screw to the rod in the desired position. This system therefore allows the pedicle screws to be slid as desired relative to one another (distraction movement) and orientated relative to one another (angular correction) so as to return the vertebrae to the desired position for osteosynthesis before the screws are rigidly fixed to the rod. However, this system which makes the distraction movements of the pedicle screws easy, does not allow for easy and precise adjustment of the mutual separation and mutual angular orientation of the pedicle screws.

Document DE 91/12466 discloses positioning equipment for an osteosynthesis device. This equipment comprises two arms designed to be attached to two pedicle screws in such a way as to form extensions thereof. It also comprises an arm linking member extending from one of the arms to the other. This member has two threaded rods collaborating with the arms through screw-nut links. Manipulation of the linking member allows the distance between the arms to be varied and, by collaboration with the screw linking member, allows the relative inclination of the screws to be varied. However, this device has the drawback that manipulating the threaded member is a relatively lengthy process, particularly when there is a desire to produce a large variation in the distance between the arms. Furthermore, this lengthy manipulation requires the operator to perform numerous operations on the equipment, particularly repetitive turns of the arm linking member. All these operations may induce stresses which are transmitted as far as the vertebrae.

One object of the invention is to provide equipment that allows the relative position of the arms to be varied more quickly while at the same time avoiding transmitting undesirable stresses to the vertebrae.

With a view to achieving this objective, the invention provides positioning equipment for an osteosynthesis system for a spinal column comprising two elongate anchoring members each designed to be anchored in a vertebra of the column, and an elongate anchoring linking element designed to connect the anchoring members together, the system being designed to have an unlocked configuration in which each anchoring member can turn with respect to the anchoring linking element about a first axis perpendicular to a longitudinal direction of the anchoring member and perpendicular to a longitudinal direction of the anchoring linking element, and a locked configuration in which each anchoring member is rigidly fixed to the anchoring linking element, the equipment comprising two arms designed to be fixed removably to the two respective anchoring members and an elongate arm linking element designed to connect part of each arm together, the arm linking element being designed to connect the arm parts, defining an extremum for the mutual separation of the arm parts, the arm linking element comprising at least one rack which has teeth designed to mesh with one of the arm parts, the at least one rack being fixed, with the ability to rotate, to the other arm part.

Thus, the rack allows the distance between the two arm parts connected by the rack to be varied very quickly. To achieve this, all that is required is for the rack to be manipulated to disengage it from one of the arms, then for the relative position of the arms to be altered before bringing the rack back into engagement with this arm. Prolonged manipulation of the equipment is avoided. In this way, numerous and repeated operations are avoided and the risk of adjustment stresses being transmitted to the vertebrae is reduced. The rack can very easily be engaged with or disengaged from the arm.

The invention provides equipment that allows precise adjustment of the mutual separation and mutual angular orientation of the pedicle screws to be performed easily. Furthermore, the anchoring linking element in particular allows for the distraction movements of the anchoring members and allows the separation between the first parts of the members connected to this linking element to be fixed. The arm linking element makes it possible to limit the separation between the arm parts. Given that the relative angular orientation of the anchoring members is the result of the choice of the separation between the first parts of the anchoring members and the choice of the separation between the arm, parts, the relative angular orientation of the anchoring members can be chosen easily and precisely. Likewise, the mutual separation between the anchoring members can be easily and precisely adjusted.

Advantageously, the arm linking element is designed such that when it defines the extremum, it allows a relative displacement of the arm parts, in just one direction of travel.

Advantageously, the arm linking element is designed such that when it defines the extremum, each arm can rotate with respect to the arm linking element about a second axis parallel to the first axis.

Advantageously, the extremum is a maximum.

Advantageously, the at least one rack is arranged such that the teeth extend toward the anchoring members when the arm parts are connected by the rack.

Advantageously, the at least one rack is able to slide with respect to the arm to which it is fixed, in the direction of the associated second axis.

Advantageously, the arm part designed to engage with the at least one rack has, for the at least one rack, a zone that is designed to engage with the rack and has a width which exceeds the width of the rack.

Advantageously, the arm bearing the at least one rack comprises means for returning the rack or racks to a position that corresponds to the meshing of the teeth with the other arm part.

Advantageously, the arm linking element comprises two racks rigidly fixed to one another, coplanar, parallel to one another, having teeth extending in the one same direction, and designed to extend one on each side of the arm with which they engage.

Advantageously, each arm is designed to be able to rotate with respect to the associated anchoring member about a longitudinal axis of the anchoring member.

Advantageously, each anchoring member comprises means of locking the anchoring member in position on the anchoring linking element, the associated arm having an aperture for actuating the locking means when the arm is fixed to the anchoring member.

Advantageously, each arm has a planar external face designed to lie facing the other arm when the arms are connected by the arm linking element, this face being adjacent to a free end of the arm which is at the opposite end from the anchoring member and being inclined with respect to a longitudinal axis of the arm so that the arm has a width which tapers toward this free end.

Advantageously, it comprises a hand tool for moving the respective parts of the anchoring members or of the arms connected by one of the linking elements closer together or further apart.

There is also provided, according to the invention, a osteosynthesis set for a spinal column, comprising an osteosynthesis system comprising two elongate anchoring members each designed to be anchored in a vertebra of the column, and an elongate anchoring linking element designed to connect the anchoring members together, the system being designed to have an unlocked configuration in which each anchoring member can turn with respect to the anchoring linking element about a first axis perpendicular to a longitudinal direction of the anchoring member and perpendicular to a longitudinal direction of the anchoring linking element, and a locked configuration in which each anchoring member is rigidly fixed to the anchoring linking element, the set furthermore comprising equipment according to the invention.

Advantageously, the anchoring linking element is designed such that in the unlocked configuration each anchoring member can slide along the anchoring linking element.

Advantageously, the anchoring linking element comprises a rod and each arm has at least one cutout for the passage of the rod, the width of the cutout exceeding a diameter of the rod.

Other features and advantages of the invention will become more apparent from the description which will follow of a preferred embodiment which is given by way of nonlimiting example. In the appended drawings:

FIG. 3 and FIG. 4 are views from the back and from the left of the rack tube of FIGS. 1 and 2;

FIG. 5 is a partial sectioned view on a larger scale of the rack tube of FIG. 4, showing the shaft and the associated spring in section at right angles to the axis of the shaft;

Figure 1:
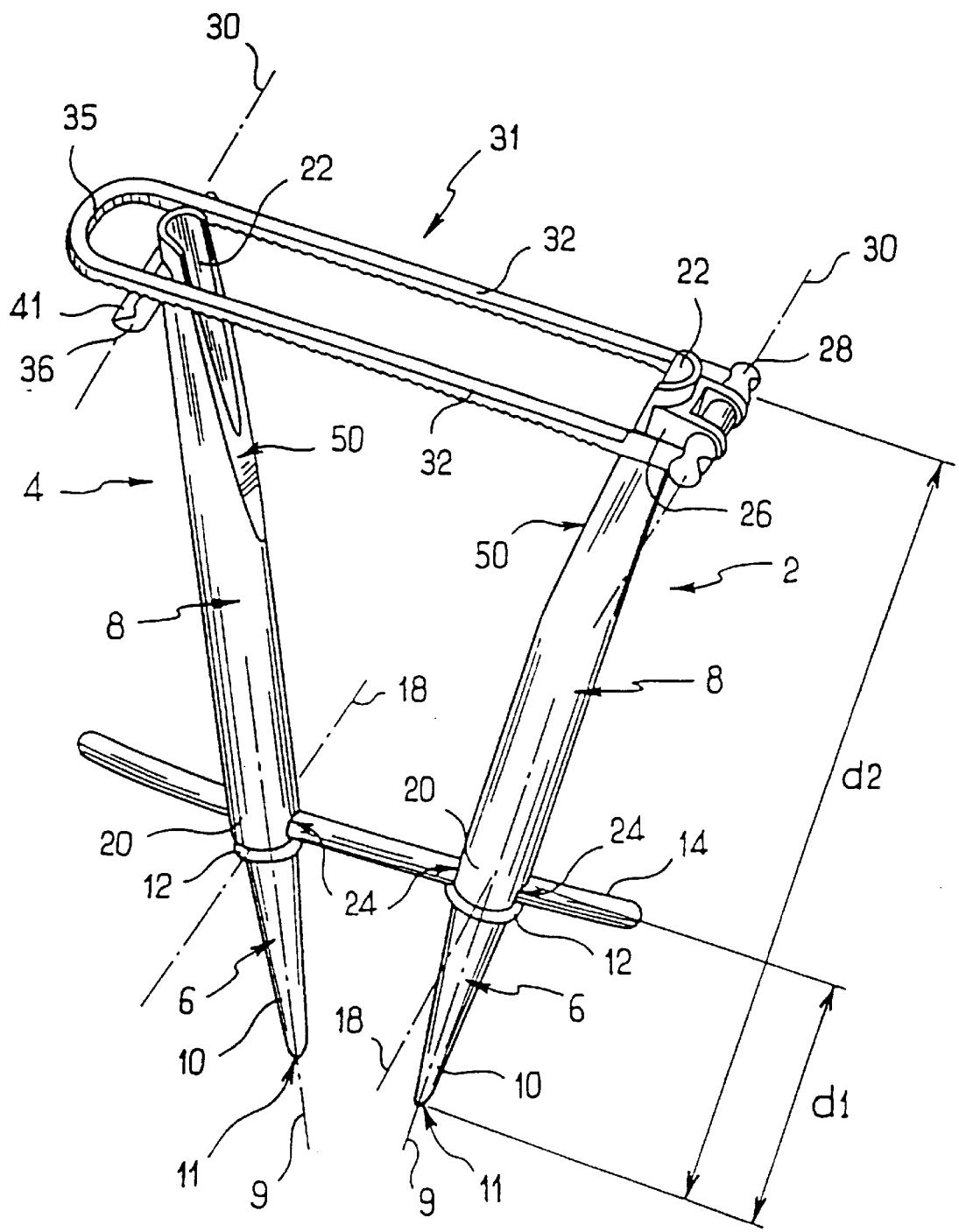
FIG. 1 is a view in perspective of the system according to the invention once installed, the vertebrae not being depicted.
Figure 2:
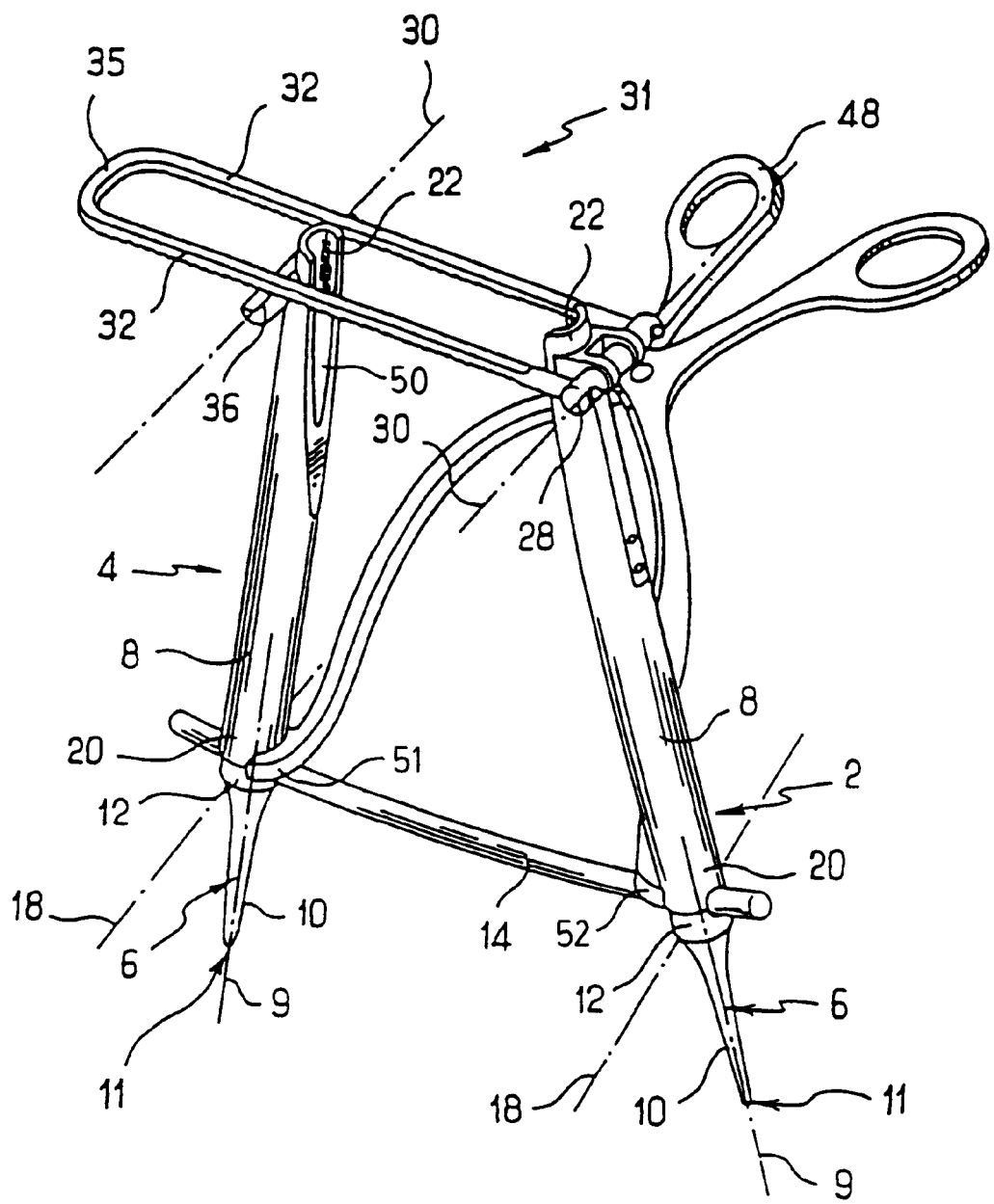
FIG. 2 is a similar view showing the installation of the system of FIG. 1, with the distraction pliers.

FIGS. 6 and 7 are views from above of the rack tube of FIG. 4, showing various translational positions of the arm linking element with respect to the associated tube along the axis of the shaft; and FIGS. 8 and 9 are views from the back and from the left of the return tube of FIGS. 1 and 2.

The osteosynthesis equipment of the invention comprises two sets like the one which has just been described with reference to the figures, including two systems intended to be fixed, for example, to the same vertebrae of the column, one on each side of the median axis of the spinal column.

The system comprises two anchoring members 6 or pedicle screws of elongate straight shape with longitudinal axis 9. Each pedicle screw 6 has a threaded end portion 10 or root intended to be anchored in a vertebra of the column, and a head 12 which is longitudinally opposed to this threaded portion 10. The screw 6 has a free end 11 longitudinally at the opposite end to the head 12.

The system comprises an anchoring linking element 14 which here consists of a generally straight elongate rod of circular cross section.

Each screw head 12 comprises, and this is not depicted, two tabs extending one opposite the other, defining a cavity between them. The head 12 comprises a radially split collar with a spherical external face and a cylindrical central bore. The collar is designed to be slipped over the rod 14 and accommodated in the cavity of the screw head 12. The screw 6 comprises a locking ring, not depicted, collaborating with the tabs by being slipped over these to maintain the separation of the tabs as they are parted by the tightening action of an internal locking nut screwed into the screw head and pressing against the split spherical collar slipped over the rod 14. After locking, the screw head is immobilized by the combined action of the internal nut and of the locking ring. Before locking, each pedicle screw 6 is free to move with respect to the rod 14, particularly by sliding along the rod and to rotate about the collar, forming a ball joint connection. In particular, the screw 6 is free to move with respect to the rod 14 by rotating about a first axis 18 perpendicular to the longitudinal axis 9 of the screw 6 and perpendicular to the longitudinal direction of the rod 14. Thus, the system may have an unlocked configuration in which the anchoring members 6 are able to move with respect to the rod 14, and a locked configuration in which the anchoring members are rigidly fixed to the rod. The unlocked configuration allows the position of the anchoring members to be chosen on the basis of the desired position for the associated vertebrae, and the locked configuration allows the vertebrae to be rigidly immobilized in this position with a view to osteosynthesis. The pedicle screws 6 and the rod 14 are generally known per se, for example from the aforementioned document FR-2 659 546 and will not be described in greater detail here.

The equipment comprises two arms 8 intended to be associated with the respective screws and each having a straight elongate overall shape of axis 9. Each arm 8 comprises a tube of cylindrical overall shape, particularly having a cylindrical external face. The arm has a lower axial end 20 and an upper axial end 22. The lower axial end 20 internally has two concentric bores of axis 9 so that the lower axial end 20 of the arm 8 can be fixed by push-fitting over the associated screw head 12. The arm 8 is thus designed to be fixed to the screw head 12 while at the same time acting as an extension of the screw. The upper axial end 22 of the arm 8 therefore extends to a distance d2 from the free end 11 of the screw 6, the distance being twice the distance d1 separating the lower axial end 20 from the free end 11 of the screw.

The lower axial end 20 has two cutouts 24 extending into the wall of the tube and which are diametrically opposed on each side of the axis 9. These cutouts are designed to house the rod 14 when the arm 8 is mounted on the screw 6. Each cutout 24 has a width substantially greater than the diameter of the rod 14 so that when the rod 14 is housed in the cutouts, the arm 8 can be rotated about the axis 9 with respect to the screw 6 through a small angle, for example 10°, each side of a central relative position, and therefore through 20° in total. Each upper axial end 20 has a central opening allowing a tool to be slipped into the arm 8 to operate the locking nut of the pedicle screw 6 on the rod 14 as mentioned earlier when the arm 8 is in place on the screw head 12.

One of the arms 8, located to the right in FIG. 1 and depicted in FIGS. 3 to 7, bears, near its upper axial end 22, a yoke 26 through which there passes a shaft 28 of axis 30 able to rotate with respect to the yoke about the axis 30 and capable of translational movement with respect to the yoke along the axis 30. We shall call this axis the "second axis". The second axis 30 is perpendicular to the longitudinal axis 9 and to the longitudinal direction of the rod 14. The second axis 30 is parallel to the first axis 18. The system comprises two racks 32 each having a series of teeth 34. These racks are straight, mutually parallel and coplanar. The teeth 34 of the two racks 32 have coincident identical profiles. The two racks are fixed with respect to each other, the racks being defined on two mutually parallel branches of a bar bent into the shape of a U. The base 35 of the U extends at a first end of the racks, and a second end of the racks is fixed rigidly to the shaft 28. The racks 32 and the shaft 28 constitute an arm linking element 31 of the system. This linking element is able to rotate with respect to one of the arms 8 about the second axis 30 and fixed permanently to this arm. In what follows, we shall call the tube that bears the racks the "rack tube".

As shown in FIGS. 7 and 8, the yoke 26, the shaft 28 and the racks 32 are configured in such a way that the shaft 28 is capable of a translational movement along the second axis 30 with respect to the arm 8 which bears it. The amplitude of this translational movement is, for example, 10 mm. FIG. 7 shows an extreme translational position of the shaft, one of the racks resting against the arm 8. FIG. 8 shows a central position, the racks 32 being equidistant from the arm 8.

The other arm 8, which lies to the left in FIG. 1 and is depicted in FIGS. 8 and 9, bears a strip 36 fixed to this arm near its upper axial end 22. The strip extends in a direction parallel to the first axis 18. The strip 36 has a tooth-shaped profile along its entire length, the straight cusp of the tooth facing away from the associated pedicle screw 6. This profile is designed to collaborate by engagement with the teeth 34 of the racks 32 to engage with the arm linking element 31. We shall call the tube bearing the strip the "return tube". Specifically, the strip 36 has two zones 41 extending one on each side of the associated arm 8 and intended to engage with the two respective racks 32. Each zone 41 of the strip has a width 1 that exceeds the width of the associated rack 32 so that it will always remain in engagement with the rack irrespective of the translational position of the rack along the second axis 30. There are two positions in which the arm linking element 31 extends in a direction substantially perpendicular to the longitudinal axis 9 of the rack tube.

In one of these positions, the teeth 34 face toward the associated pedicle screw 6 and may therefore engage with the strip 36 of the return tube.

The teeth 34 of the racks have an asymmetric right-triangle-shaped profile allowing the strip 36 to travel along the racks 32 in a first direction when the strip is engaged with the racks, and preventing it from traveling in a second direction which is the opposite of the first direction. Thus, the arm linking element 31 makes it possible to define an extremum for the mutual separation of the two upper axial ends 22 of the arms 8. In this particular instance, when the strip is engaged with the racks, the profile of the teeth allows the upper axial ends 22 of the arms to move closer together and prevents them from being moved further apart, and does so irrespective of the position of the strip along the racks. The arm linking element 31 therefore here defines a maximum for mutual separation.

The rack tube comprises a spring 40 consisting of an elongate and generally straight flat leaf extending parallel to the longitudinal axis 9, having a lower axial end 42 fixed to a central portion of the cylindrical external face of the arm 8, and an upper axial end 44 resting against the shaft 28 and arranged between the shaft 28 and the arm. The shaft 28 has two flats 46, 48 running substantially at right angles to one another and parallel to the second axis 30. The remainder of the face of the shaft 28 is cylindrical. The flat 46 is situated in such a way that it makes surface-to-surface contact with the spring 40 when the racks 32 lie at right angles to the arm 8 which bears it with a view to engaging with the strip 36. The spring 40 and the flat 46 constitute means of returning the arm linking element 31 to a position in which the racks engage with the strip. Likewise, the second flat 48 is situated in such a way that the arm linking element 31 is returned to a position of rest wherein it runs substantially parallel to the longitudinal axis 9, resting against the cylindrical face of the arm 8, this position of rest being separated from the aforementioned engagement position by an angle of about 270°.

The equipment furthermore comprises a hand tool such as distracting pliers 48 which have two actuating ends 50 designed to be pressed simultaneously against the lower axial end 20 of the arms 8 with a view to separating them.

The strip 36 and the yoke 26 are arranged in such a way that when the two arms 8 are connected by the arm linking element 31, the strip and the yoke extend on a rear side of each arm, facing away from the other arm. Each arm 8 has a flat external face 50 extending from a central zone of the arm as far as the upper axial end 22. This face 50 is inclined with respect to the longitudinal axis 9 so that the upper axial end portion 22 of the arm has a width which tapers toward this end 22. These flat faces 50 are arranged in such a way that they lie facing one another when the two arms are connected by the arm linking element 31. The flat faces 50 are respectively on the opposite side to the yoke 26 and to the strip 36 with respect to the longitudinal axis 9.

The arm linking element 31 and the two arms 8 constitute equipment for positioning the osteosynthesis system.

The set is used as follows. Each pedicle screw 6 is fixed to vertebrae in the column, or to parts of vertebrae. The collars and the rod 14 are fitted, the set being in the unlocked configuration. Each arm 8, namely the rack tube and the return tube, is mounted over the associated screw 6. Using the pliers 48, the lower axial ends 20 of the arms 8 are parted so as to bring about a distraction movement of the vertebrae associated with the anchoring members 2, 4. The rod 14 therefore acts as a guide for the relative movement of the anchoring members. Next, keeping the lower axial ends 20 in this position, the arm linking element 31 is moved from its position of rest resting against the arm 8 into the position of engagement with the strip 36.

The two upper axial ends 22 are then manually brought closer together as allowed by the racks 32 in engagement with the strip 36, to adjust and choose the maximum separation between the upper axial ends of the arms. During this movement closer together, the relative angular orientation of the longitudinal axes 9 of the anchoring members 6 varies. Thus is performed a movement that corrects the angular position of the vertebrae.

When the desired separation between the upper axial ends 22 is reached, these ends 22 are released. The racks 32 then prevent any mutual separation of the ends 22 in this position (unless the racks are disengaged from the strip). It is therefore possible, as need be, to alter the mutual separation between the lower axial ends 20 again, for example using the pliers 48, to perform a further distraction movement and angular correction and thus define the relative position of the vertebrae even more explicitly. During this movement, the upper axial ends 22 keep the same mutual separation as a result of the inherently static nature of the link between the racks 32 and the strip 36. All that happens is that the rack tube rotates with respect to the arm linking element 31 about the associated second axis 30, and that the return tube rotates with respect to the arm linking element 31 about the associated second axis 30 defined by the cusp of the tooth of the strip 36 that is engaged with the racks 32. This second axis 30 of the return tube is parallel to the second axis 30 of the rack tube. It is possible thereafter and as required, to displace the upper axial ends 22 of the arms 8 relative to one another either bringing them closer to one another with the strip 36 still engaged with the racks 32, or moving them further apart by temporarily disengaging strip and rack.

When the racks 32 are engaged with the strip 36, they extend on each side of the arm 8. Thus, as the strip 36 travels along the racks to move the ends 22 closer together, the racks constitute a guide for the movement of the arm 8 bearing the strip. The two inclined faces 50 allow the two upper axial ends 22 to be brought very close together, for example by bringing them into contact with one another.

Once the desired position of the vertebrae has been reached, the pedicle screws 6 are locked rigidly in position on the rod 14 using the aforementioned opening made in the arms for this purpose. The arms 8 are then removed by detaching them from the respective pedicle screws 6.

The freedom of each arm 8 to rotate with respect to the associated screw 6, and the freedom of the shaft 28 to effect translational movement with respect to the yoke 26 allows the system to adapt to the desired positions of the vertebrae.

The equipment could comprise several pairs of anchoring members 6 and arms 8. It could comprise one or more rods 14 for connecting these members together.

The teeth 34 of each rack 32 could face in the opposite direction, with a view to defining a minimum separation between the upper axial ends 22 of the arms.

In this instance, the length of the arm 8 is about twice the length of each pedicle screw 6. The length of the arm will advantageously be greater than the length of the associated screw 6.

The equipment according to the invention may be employed using an osteosynthesis device different than the one in patent document FR-2 659 546.

Furthermore, it is possible, in general, to envisage positioning equipment for an osteosynthesis system for a spinal column comprising two anchoring members each designed to be anchored in a vertebra of the column, and an anchoring linking element designed to connect the anchoring members together, the system being designed to have an unlocked configuration in which each anchoring member can move with respect to the anchoring linking element, and a locked configuration in which each anchoring member is rigidly fixed to the anchoring linking element, the equipment comprising two arms designed to be fixed removably to the two respective anchoring members 6 and an arm linking element 31 designed to connect part of each arm together, in which each arm has an aperture for actuating position-locking means provided on each anchoring member while the arm is fixed to the anchoring member.

As a preference, this aperture will extend along the axis of the arm, which will therefore be hollow, so that the locking means located close to the base of the arm can be actuated by introducing a tool into the arm from the top of the arm.

Furthermore, one might also more generally envisage positioning equipment for an osteosynthesis system for a spinal column comprising two anchoring members each designed to be anchored in a vertebra of the column, and an anchoring linking element designed to connect the anchoring members together, the system being designed to have an unlocked configuration in which each anchoring member can slide along the anchoring linking element, and a locked configuration in which each anchoring member is rigidly fixed to the anchoring linking element, the equipment comprising two arms designed to be fixed removably to the two respective anchoring members and an arm linking element designed to connect part of each arm together. Consequently, the equipment will also advantageously comprise a hand tool such as the tool 48.

What is claimed is:

1. Positioning equipment for an osteosynthesis system for a spinal column comprising two elongate anchoring members (6) each designed to be anchored in a vertebra of the column, and an elongate anchoring linking element (14) designed to connect the anchoring members together, the system being designed to have an unlocked configuration in which each anchoring member (6) can turn with respect to the anchoring linking element (14) about a first axis (18) perpendicular to a longitudinal direction (9) of the anchoring member and perpendicular to a longitudinal direction of the anchoring linking element (14), and a locked configuration in which each anchoring member (6) is rigidly fixed to the anchoring linking element (14), the equipment comprising two arms (8) designed to be fixed removably to the two respective anchoring members (6) and an elongate arm linking element (31) designed to connect part (26, 36) of each arm together, wherein the arm linking element is designed to connect the arm parts, defining an extremum for the mutual separation of the arm parts (26, 36), the arm linking element (31) comprising at least one rack (32) which has teeth (34) designed to mesh with one (36) of the arm parts, the at least one rack being fixed, with the ability to rotate, to the other arm part (26).

2. The positioning equipment according to claim 1, wherein the arm linking element (31) is designed such that when it defines the extremum, it allows a relative displacement of the arm parts (26, 36) in just one direction of travel.

3. The positioning equipment according to either one of claims 1 and 2, wherein the arm linking element (31) is designed such that when it defines the extremum, each arm (8) can rotate with respect to the arm linking element (31) about a second axis (30) parallel to the first axis (18).

4. The positioning equipment according to any one of claims 1 to 3, wherein the extremum is a maximum.

5. The positioning equipment according to any one of claims 1 to 4, wherein the at least one rack (32) is arranged such that the teeth (34) extend towards the anchoring members (6) when the arm parts (26, 36) are connected by the rack (32).

6. The positioning equipment according to any one of claims 1 to 5 wherein the at least one rack (32) is able to slide with respect to the arm (8) to which it is fixed, in the direction of the associated second axis (30).

7. The positioning equipment according to any one of claims 1 to 6 wherein the arm part (36) designed to engage with the at least one rack (32) has, for the at least one rack, a zone (41) that is designed to engage with the rack and has a width (1) which exceeds the width of the rack.

8. The positioning equipment according to any one of claims 1 to 7, wherein the arm (8) bearing the at least one rack (32) comprises means (40) for returning the rack or racks to a position that corresponds to the meshing of the teeth (34) with the other arm part (36).

9. The positioning equipment according to any one of claims 1 to 8 wherein the arm linking element (31) comprises two racks (32) rigidly fixed to one another, coplanar, parallel to one another, having teeth (34) extending in the one same direction, and designed to extend one on each side of the arm with which they engage.

10. The positioning equipment according to any one of claims 1 to 9 wherein each arm (8) is designed to be able to rotate with respect to the associated anchoring member (6) about a longitudinal axis (9) of the anchoring member.

11. The positioning equipment according to any one of claims 1 to 10 wherein each arm (8) has an aperture for introducing a tool for actuating a position locking means provided on each anchoring member (6) while the arm is fixed to the anchoring member.

12. The positioning equipment according to any one of claims 1 to 11, wherein each arm (8) has a planar external face (50) designed to lie facing the other arm when the arms are connected by the arm linking element (31), this face being adjacent to a free end (22) of the arm which is at the opposite end from the anchoring member (6) and being inclined with respect to a longitudinal axis (9) of the arm so that the arm has a width which tapers toward this free end (22).

13. The positioning equipment according to any one of claims 1 to 12, wherein it further comprises a hand tool (48) for moving the respective parts (12) of the anchoring members (6) or of the arms (8) connected by one of the linking elements closer together or further apart.

14. An osteosynthesis set for a spinal column, comprising an osteosynthesis system comprising two elongate anchoring members (6) each designed to be anchored in a vertebra of the column, and an elongate anchoring element (14) designed to connect the anchoring members together, the system being designed to have an unlocked configuration in which each anchoring member (6) can turn with respect to the anchoring linking element (14) about a first axis (18) perpendicular to a longitudinal direction (9) of the anchoring member and perpendicular to a longitudinal direction of the anchoring linking element (14), and a locked configuration in which each anchoring member (6) is rigidly fixed to the anchoring linking element (14), and equipment according to any one of claims 1 to 13.

15. The osteosynthesis set according to claim 14, wherein the anchoring linking element (14) is designed such that in the unlocked configuration each anchoring member (6) can slide along the anchoring linking element (14).

16. The osteosynthesis set according to either one of claims 14 or 15, wherein the anchoring linking element (14) comprises a rod and each arm (8) has at least one cutout (24) for the passage of the rod, the width of the cutout exceeding a diameter of the rod.

* * * * *